(12) United States Patent
Gréco

(10) Patent No.: US 12,005,034 B2
(45) Date of Patent: *Jun. 11, 2024

(54) TOPICAL PHARMACEUTICAL COMPOSITION COMPRISING AT LEAST AMITRIPTYLINE, FOR THE TREATMENT OF PERIPHERAL NEUROPATHIC PAIN

(71) Applicant: ALGOTHERAPEUTIX, Suresnes (FR)

(72) Inventor: Céline Gréco, Paris (FR)

(73) Assignee: ALGOTHERAPEUTIX, Suresnes (FR)

( * ) Notice: Subject to any disclaimer, the term of this patent is extended or adjusted under 35 U.S.C. 154(b) by 343 days.

This patent is subject to a terminal disclaimer.

(21) Appl. No.: 16/898,249

(22) Filed: Jun. 10, 2020

(65) Prior Publication Data

US 2020/0297663 A1    Sep. 24, 2020

Related U.S. Application Data

(63) Continuation-in-part of application No. 16/608,783, filed as application No. PCT/EP2018/059948 on Apr. 18, 2018.

(30) Foreign Application Priority Data

Apr. 25, 2017   (FR) ..................... 1753577

(51) Int. Cl.
| | | |
|---|---|---|
| *A01N 37/00* | (2006.01) | |
| *A01N 25/00* | (2006.01) | |
| *A01N 37/12* | (2006.01) | |
| *A01N 37/44* | (2006.01) | |
| *A61K 9/00* | (2006.01) | |
| *A61K 9/06* | (2006.01) | |
| *A61K 31/135* | (2006.01) | |
| *A61K 31/215* | (2006.01) | |
| *A61K 31/24* | (2006.01) | |
| *A61P 23/02* | (2006.01) | |

(52) U.S. Cl.
CPC .......... *A61K 31/135* (2013.01); *A61K 9/0014* (2013.01); *A61K 9/06* (2013.01); *A61P 23/02* (2018.01)

(58) Field of Classification Search
None
See application file for complete search history.

(56) References Cited

U.S. PATENT DOCUMENTS

| | | |
|---|---|---|
| 2002/0028789 A1 | 3/2002 | Ford |
| 2004/0101582 A1 | 5/2004 | Wolicki |
| 2005/0209220 A1 | 9/2005 | Conforti |
| 2011/0065627 A1 | 3/2011 | Barathur et al. |

FOREIGN PATENT DOCUMENTS

| | | |
|---|---|---|
| WO | 03/015699 A2 | 2/2003 |
| WO | 2017106714 A1 | 6/2017 |
| WO | 2018106107 A1 | 6/2018 |
| WO | 2018106108 A1 | 6/2018 |

OTHER PUBLICATIONS

Kopsky et al., "Topical phenytoin for the treatment of neuropathic pain," Journal of Pain Research, Feb. 27, 2017, pp. 469-473, 5 pages.
Barton, D.L., et al., "A Double-Blind, Placebo-Controlled Trial of a Topical Treatment for Chemotherapy-Induced Peripheral Neuropathy: NCCTG Trial No. 6CA," Support Care Cancer 19:833-841, 2011.
Gewandter, J.S., et al., "A Phase III Randomized, Placebo-Controlled Study of Topical Amitriptyline and Ketamine for Chemotherapy-Induced Peripheral Neuropathy (CIPN): A University of Rochester CCOP Study of 462 Cancer Survivors," Support Care Cancer 22:1807-1814, 2014.
Kopsky, D.J., et al., "High Doses of Topical Amitriptyline in Neuropathic Pain: Two Cases and Literature Review," Pain Practice 12(2):148-153, 2012.
International Search Report dated Jul. 24, 2018, issued in corresponding International Application No. PCT/EP2018/059948, filed Apr. 18, 2018, 6 pages.
Office Action dated Mar. 16, 2023, issued in corresponding U.S. Appl. No. 16/608,783, filed Oct. 25, 2019, 18 pages.

*Primary Examiner* — Layla Soroush
(74) *Attorney, Agent, or Firm* — Sheridan Ross P.C.

(57) ABSTRACT

The present disclosure relates to a pharmaceutical composition comprising from 10% to 30% by weight of amitriptyline or of a pharmaceutically acceptable salt or ester thereof, relative to the total weight of the composition, amitriptyline, for use in the topical treatment of chemotherapy-induced peripheral neuropathic pain.

5 Claims, 7 Drawing Sheets

TOPICAL PHARMACEUTICAL COMPOSITION COMPRISING AT LEAST AMITRIPTYLINE, FOR THE TREATMENT OF PERIPHERAL NEUROPATHIC PAIN

CROSS-REFERENCES TO RELATED APPLICATIONS

This application is a continuation-in-part of application Ser. No. 16/608,783, filed Oct. 25, 2019, which is a U.S. National Stage of PCT/EP2018/059948, filed Apr. 18, 2018, which claims the benefit of French Application No. 1753577, filed Apr. 25, 2017, the entire disclosures of said applications are hereby incorporated by reference herein.

BACKGROUND

The present invention relates to a pharmaceutical composition comprising from 10% to 30% by weight, relative to the total weight of the composition, of amitriptyline or of a pharmaceutically acceptable salt thereof, for use in the topical treatment of chemotherapy-induced peripheral neuropathic pain.

Peripheral neuropathic pain is caused by damage to nerve structures such as peripheral nerve endings or nociceptors which become extremely sensitive to stimulation and which can generate pulses in the absence of stimulation.

This damage can occur for many reasons, such as trauma, diseases such as diabetes, shingles and advanced-stage cancers, chemotherapy treatments or else a chemical burn. The lesion of the peripheral nerve can result in pathological states characterized by the presence of continuous spontaneous pain which is superficial (sensation of painful burning or cold) or deep (compression or vice sensation), paroxysmal pain (electrical discharges, stabbing) with, upon clinical examination, hypoesthesia or, on the contrary, hyperalgesia (increased response to harmful stimuli), allodynia (pain induced by a non-painful stimulus) or else hyperpathia (persistent pain during normally non-nociceptive repeated stimulations). Neuropathies may also be associated with sensory signs such as paresthesia, numbness, pruritis.

Chemically induced neuropathies are particularly frequent, disabling and difficult to treat. They are dose-dependent. Peripheral nerve damage represents the majority of neurological damage associated with chemotherapy toxicity. It is the consequence of direct toxic damage to the axon or of demyelination and represents the most frequent limiting factor after haematological toxicity.

Thus, before chemically induced neuropathies occur, the chemotherapy doses will be reduced or the treatment may even be stopped, thus constituting an actual reduction in the patient's chances.

Thus, it has been possible to observe neuropathies subsequent to treatment with alkaloids (vincristine, vinblastine, vinorelbine) often leading to small-fibre damage, platinum derivatives (oxaliplatin, cisplatin, carboplatin), anti-topoisomerases (VP16), proteasome inhibitors (bortezomib, carfilzomib), thalidomide derivatives such as lenalidomide, taxanes such as taxol or taxotere which instead affect large fibres. There are also neuropathies after treatment by immunotherapy, such as for example anti-CD20, anti-CD30, anti-CD38.

This chemically induced pain occurs according to poorly understood mechanisms, thus certain authors think that it is due to a direct toxic effect on the sensory axon, to demyelination or else to an impairment of calcium metabolism, associated with damage to mitochondria, the site of action of paclitaxel and of vincristine, for example.

Thus, it is known that taxanes intervene on the spinal ganglion, the microtubules, the mitochondria and the nerve endings, platinum salts intervene on myelin and ion channels, while alkaloids intervene on myelin and microtubules.

This neuropathic pain is often refractory to the usual analgesic treatments and leads to decreases in doses or even interruptions of chemotherapy. It is at the current time treated with per os treatments comprising antidepressants (Amitriptyline, Duloxetine, Venlafaxine, etc.) and/or anti-epileptics (Gabapentin, Pregabalin). Unfortunately, these systemic treatments induce major side effects (dizziness, drowsiness, memory loss, dryness of the mouth or even urine retention, nausea, etc.) leading to poor treatment adherence and pain control which is not very satisfactory.

This pain mostly affects the extremities of the hands and feet and leads to a considerable impairment of the quality of life of patients with a functional impotence that can range up to the inability to walk, gripping difficulties, impaired sleep, the occurrence of a depressive syndrome or even a suicidal tendency. The impact on the social and professional life can also be very significant.

The intensity of the pain is often described as severe with patients who evaluate their pain at more than 7/10 on the visual analogue scale (pain graded from 0 to 10).

Chemotherapy-induced neuropathic pain is essentially toxic in origin, as recalled above, whereas post-shingles neuropathies are generally linked to nerve damage owing to a prior infection by the herpes zoster virus. The damaged nerves are no longer capable of correctly transmitting the signals from the skin to the brain. Tricyclic antidepressants are chemical compounds discovered at the beginning of the 1950s. They are widely used to treat various psychiatric disorders, in particular depression, panic disorders, obsessive compulsive disorders, enuresis in children, bipolar disorders and hyperactivity. They are also used as analgesics.

These compounds are generally administered orally.

Amitriptyline is a tricyclic antidepressant discovered in 1960, which has frequently been recommended as first-line treatment for major depression, post-traumatic stress disorder (PTSD), generalized anxiety disorder (GAD), social phobia (SP), panic disorder, fibromyalgia, chronic musculoskeletal pain, akinesia in Parkinson's disease, cataplexy, migraines, Parkinson's disease, vasomotor symptoms of the menopause, nocturnal enuresis, premenstrual dysphoric disorder (PMDD), bipolar disorder, bulimia, obsessive compulsive disorders (OCD) and neuropathic pain.

In the past, patients were generally treated by administering analgesics to relieve the pain. The oral route was widely preferred.

However, the oral administration of amitriptyline, as for all tricyclic antidepressants, has many side effects linked to their anti-cholinergic effects (risk of arterial hypotension, sinus tachycardia or supraventricular tachycardia, in rare cases AVB, blurred vision, dryness of the mouth, skin flushes, acute urine retention or slowing of transit), anti-α-adrenergic effects (risk of sedation, of hypotension, of impotence), sympathetic reflex central inhibitor or else membrane-stabilizing effects (pro-arythmogenic effect). In particular, one of the formidable and feared effects of amitriptyline is QT prolongation that can lead to the death of a patient who has not been correctly monitored.

In particular, during oral administration of amitriptyline for the treatment of diabetic neuropathic pain, cases of sedation, of orthostatic hypotension and of anti-cholinergic effects have been reported (cf. in particular Kiani et al, Iran J Pharm. Res. 2015 Fall; 14(4):1263-8). In the long term, patients report memory problems, difficulties in concentration with considerable effects on the quality of their work or on their daily life.

Moreover, the efficacy of orally administered amitriptyline is slow (5 to 7 days of treatment are required in order to be able to begin to assess the efficacy of the product), variable according to patients and incomplete. It is consequently often necessary to use combinations of analgesics in order to overcome these drawbacks.

In addition, taking tricyclic antidepressants orally often has a bad reputation with patients because of their uses in various psychiatric disorders.

Given the problems of oral treatments, topical treatments have been attempted. The efficacy of amitriptyline administered topically for neuropathic pain has not been demonstrated. In particular, the article by Thompson et al., "Systematic review of topical amitriptyline for the treatment of neuropathic pain", J. Clin. Pharm. Therm. 2015, 40, 496-503, concludes that controlled clinical trials reveal that topical amitriptyline is not efficacious in the treatment of neuropathic pain. The maximum dose used is 5% for a patient suffering from multiple sclerosis and exhibiting neuropathic pain. Likewise, the article "A phase III randomized, placebo-controlled study of topical amitriptyline and ketamine for chemotherapy-induced peripheral neuropathy", Support Care Cancer, 2014 July; 22(7):1807-1814, concluded that a topical composition comprising 2% by weight of ketamine and 4% by weight of amitriptyline was not efficacious for treating post-chemotherapy neuropathic pain.

Thus, there is no satisfactory treatment for chemotherapy-induced neuropathic pain. Furthermore, treatments combining ketamine and amitriptyline, which appeared to give results in patients with post-shingles neuropathic pain or neuropathic pain of diabetic origin, have not made it possible to overcome chemotherapy-induced neuropathic pain, as noted in the abovementioned phase III clinical study.

Moreover, the doses envisaged, despite the disabling nature of this pain, have never exceeded 5%, whether orally or topically.

Moreover, patients suffering from neuropathies in the extremities (feet and hands) often exhibit damaged or even chapped and dried skin.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present disclosure relates to a pharmaceutical composition comprising from 10% to 30% by weight of amitriptyline or of a pharmaceutically acceptable salt or ester thereof, relative to the total weight of the composition, amitriptyline, for use in the topical treatment of chemotherapy-induced peripheral neuropathic pain.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
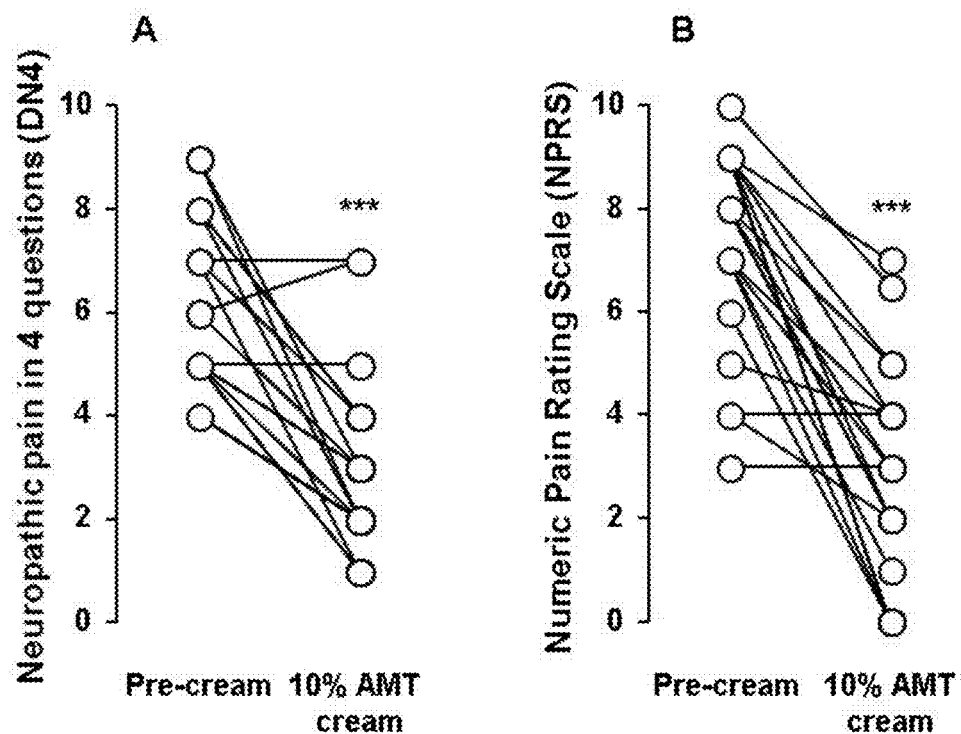
FIG. 1 chemotherapy-induced hand and/or foot pain is alleviated by local 10% amitriptyline application.

A subject of the invention is thus the provision of a composition based on amitriptyline which is efficacious when applied to the skin in the treatment of peripheral neuropathies and in particular of chemotherapy-induced neuropathies.

A subject of the invention is also a composition based on amitriptyline which makes it possible, in addition to overcoming neuropathic pain, to return to a healthier and more hydrated skin.

Other subjects of the invention will emerge on reading the description and the examples which follow.

It has been discovered, surprisingly, that a pharmaceutical composition for topical application comprising, in a pharmaceutically acceptable support suitable for topical application, at least 10% by weight of amitriptyline or of a pharmaceutically acceptable salt thereof, administered topically, makes it possible to efficaciously treat chemotherapy-induced peripheral neuropathic pain (or CIPN for chemotherapy-induced peripheral neuropathy).

A subject of the invention is thus a pharmaceutical composition comprising, in a pharmaceutically acceptable support suitable for topical application, from 10% to 30% by weight, relative to the total weight of the composition, of amitriptyline or of a pharmaceutically acceptable salt thereof, for use in the topical treatment of chemotherapy-induced peripheral neuropathic pain.

Topical application of the composition according to the invention is an efficacious treatment for chemotherapy-induced peripheral neuropathic pain.

Furthermore, the topical application of the composition according to the invention exhibits few, or even exhibits no, side effects. In particular, no skin irritation is observed at the site of application of the composition.

Amitriptyline has the formula (I) below:

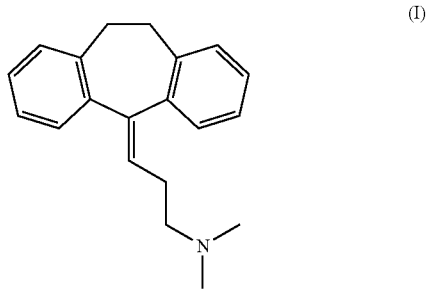 [SMILES: CN(C)CCC=C1c2ccccc2CCc2ccccc21]

(I)

In the context of the present invention, the term "pharmaceutically acceptable amitriptyline salt" is intended to mean the salts of amitriptyline compatible with a pharmaceutical composition, i.e. intended to be administered to human beings. In particular, the term "pharmaceutically acceptable amitriptyline salt" is intended to mean the hydrates, solvates, acid salts such as hydrochlorides and clathrates of amitriptyline.

Amitriptyline hydrochloride will be used as most particularly preferred amitriptyline salt.

As indicated above, the topical application of the composition according to the invention is an efficacious treatment for chemotherapy-induced peripheral neuropathic pain.

The application of the composition according to the invention, in the treatment of chemotherapy-induced neuropathic pain, has made it possible to obtain particularly spectacular results with regard to the results previously obtained. Thus, it has been possible to reduce pain classified according to the simple numerical scale between 4/10 and 7/10 according to patients to a value of virtually zero for all patients after 1 month of treatment.

The use of the composition according to the invention in the treatment of chemotherapy-induced neuropathic pain has made it possible to continue chemotherapy treatments, which would often have to be interrupted or suspended because of severe neuropathic pain.

A subject of the invention is thus also the use of the composition according to the invention in the context of a cancer treatment combining chemotherapy and treatment of neuropathic pain that may be chemotherapy induced. The composition according to the invention may thus be administered between chemotherapy regimens and may thus make it possible to continue the treatments.

The inventor has moreover discovered that the composition according to the invention can be applied preventively before a chemotherapy treatment and has, surprisingly, a neuroprotective effect, which would make it possible to reduce, or even prevent, chemotherapy-induced neuropathic pain.

The composition according to the invention can thus also be administered before beginning a chemotherapy treatment, the administration of the composition according to the invention being continued during and between the chemotherapy regimens and, if necessary, continued after the treatment depending on the state of neuropathic pain.

The composition according to the invention comprises from 10% to 30% by weight, preferably from 10% to 20% and in particular from more than 10% to 15% by weight of amitriptyline or of a pharmaceutically acceptable salt thereof relative to the total weight of the composition.

Particularly preferably, the amitriptyline is the only pharmaceutical active agent of the composition according to the invention.

In one preferred form, the composition contains the amitriptyline in the abovementioned proportions as sole pain-treating agent, in particular without any other analgesic agent or antidepressant or antiepileptic agent also sometimes recommended for the treatment of neuropathic pain, such as for example lidocaine, gabapentin, pregabalin, baclofen, capsaicin, ketamine.

This is particularly advantageous in the context of the invention since, contrary to the prior art, amitriptyline alone at a content of at least 10% by weight exhibits good efficacy in the treatment of chemotherapy-induced peripheral neuropathic pain.

It has also been noted that the application of the composition to skin explants in an ex vivo model results in a passage into the bloodstream of less than 0.1% relative to the amount of amitriptyline present in the composition. The very low passage into the bloodstream makes it possible to avoid the side effects noted for the treatments applied to neuropathies in the prior art. In particular, the bioconversion to nortriptyline is minor.

The pharmaceutical compositions according to the invention are generally in the form of an oil-in-water emulsion.

These compositions contain, as essential components, at least fatty substances, one or more hydrating active agents, non-ionic surfactants.

The oily phase of the composition according to the invention comprises one or more fatty substances.

The term "fatty substance" is intended to mean an organic compound which is water-insoluble at ambient temperature (25° C.) and at atmospheric pressure (1.013×105 Pa) (solubility less than 5% by weight, and preferably less than 1% by weight, even more preferentially less than 0.1% by weight). They have in their structure at least one hydrocarbon-based chain comprising at least 6 carbon atoms and/or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

Preferably, the fatty substance(s) are chosen from synthetic, animal, mineral or vegetable oils, silicone oils, fatty acids, fatty alcohols, waxes, gums and mixtures of these compounds.

As an example of a mineral oil, mention may be made of liquid paraffins of varied viscosities.

By way of vegetable oil, mention may in particular be made of sweet almond oil, palm oil, soybean oil, sesame oil and sunflower oil.

By way of animal oil, mention may in particular be made of lanolin, squalene, fish oil and mink oil.

By way of synthetic oil, mention may in particular be made of esters of alcohol and of fatty acid, such as cetearyl isononanoate, isopropyl palmitate and caprylic/caprylate triglycerides.

As an example of silicone oil, mention may in particular be made of dimethicone and cyclomethicone.

As an example of fatty acid, mention may in particular be made of stearic acid and palmitic acid.

As an example of fatty alcohol, mention may in particular be made of stearyl alcohol, cetostearyl alcohol and cetyl alcohol.

By way of wax, mention may in particular be made of beeswax (or cera alba), carnauba wax and candelilla wax.

By way of gum, mention may in particular be made of silicone gum.

Particularly preferably, the fatty substance(s) of the composition according to the invention are chosen from mineral oils, fatty acids, waxes and mixtures of these compounds.

Most particularly preferably, the composition according to the invention comprises a mixture of one or more mineral oils, of one or more fatty acids and of one or more waxes.

The fatty substance(s) preferably represent from 15% to 25% by weight, relative to the total weight of the composition, and in particular 20% to 25% by weight, relative to the total weight of the composition.

The composition according to the invention may also comprise one or more surfactants, which are preferably non-ionic, and which may or may not be oxyethylenated.

Particularly preferably, the composition according to the invention comprises one or more non-oxyethylenated non-ionic surfactants.

The compositions according to the invention may also contain glucolipid self-emulsifying systems, such as mixtures of fatty alcohol and of alkyl glycosides having 10 to 16 carbon atoms and in particular a mixture of cetylstearyl alcohol and cetearyl glucoside.

The non-ionic surfactant(s) can advantageously be chosen from sorbitan esters, glycerol esters, and mixtures of these compounds, polaxamers.

By way of sorbitan ester, mention may in particular be made of sorbitan stearate or sorbitan oleate.

By way of glycerol ester, mention may in particular be made of glyceryl stearate.

Preferably, the composition according to the invention comprises a mixture of one or more sorbitan esters and of one or more glycerol esters.

Advantageously, the surfactant(s) that can be used in the composition according to the invention represent, when they are present, from 2% to 8%, preferably 2% to 5% by weight, relative to the total weight of the composition.

The composition according to the invention may also comprise one or more gelling agents.

According to the invention, a gelling agent is any compound which, when added to a composition, increases the viscosity of said composition, the gelling agent representing from 0.01% to 4% by weight, preferably from 0.01% to 1% by weight, relative to the total weight of the composition.

By increasing the viscosity of the composition according to the invention, said composition is more stable over time.

The gelling agent(s) that can be used in the composition according to the invention are preferably chosen from carboxyvinyl polymers (carbomer), cellulose-based derivatives, xanthan gums, vegetable gums, aluminium/magnesium silicates, guar gums, polyacrylamide polymers, acrylate copolymers, modified starches, and mixtures of these compounds.

By way of carboxyvinyl polymer (carbomer), mention may in particular be made of Carbopol 981, Carbopol ETD 2020, Carbopol 980, Carbopol Ultrez 10 NF and Pemulen TR1, sold by Lubrizol.

By way of cellulose-based derivative, mention may in particular be made of hydroxypropylmethylcellulose and hydroxyethylcellulose.

By way of aluminium/magnesium silicate, mention may in particular be made of Veegum K and Veegum Ultra sold by Vanderbilt.

As polyacrylamide polymer, mention may in particular be made of the polyacrylamide/$C_{13-14}$ isoparaffin/laureth-7 mixture, for example that sold by SEPPIC under the brand name Sepigel 305.

By way of modified starch, mention may in particular be made of Structures Solanace sold by Akzo Nobel.

Preferably according to the invention, the gelling agent(s) that can be used according to the invention are chosen from carboxyvinyl polymers (carbomer).

The gelling agent(s) that can be used in the composition according to the invention represent, when they are present, preferably from 0.1% to 4% by weight relative to the total weight of the composition.

The composition according to the invention advantageously comprises water.

In one preferred embodiment, the composition according to the invention comprises one or more hydrating active agents.

A hydrating active agent is an active agent capable of reducing the state of dryness of an epidermis.

Thus, the term "hydrating active agent" is intended to mean generally a compound which acts on the barrier function, with a view to maintaining the hydration of the stratum corneum, or an occlusive compound.

Mention may in particular be made of ceramides, sphingoid-based compounds, lecithins, glycosphingolipids, phospholipids, cholesterol and its derivatives, phytosterols (stigmasterol, β-sitosterol, campesterol), 1,2-diacylglycerol, 4-chromanone, pentacyclic triterpenes, glycosaminoglycans, sugars, polysaccharides, urea and glycerol.

Preferably, the hydrating active agent is glycerol.

Advantageously, the hydrating active agent(s) that can be used in the composition according to the invention represent, when they are present, from 7% to 15% by weight relative to the total weight of the composition.

The composition according to the invention may also comprise one or more additives or combinations of additives chosen from preservatives, stabilizers, flavour enhancers and pH adjusters.

As preservative, mention may in particular be made of phenoxyethanol.

Of course, those skilled in the art will choose the various additives or combinations of additives while taking great care to ensure that the properties intrinsically associated with the composition according to the invention are not impaired, or are barely impaired, by the envisaged additions.

The additives, when they are present in the composition according to the invention, generally each represent from 0.001% to 20% by weight relative to the total weight of the composition.

In one preferred embodiment of the invention, the composition comprises:
  from 10% to 30%, preferably from 10% to 20% by weight, more preferentially from more than 10% to 15% by weight of amitriptyline or of a pharmaceutically acceptable salt thereof,
  from 2% to 8% by weight of one or more non-ionic surfactants,
  from 15% to 25% by weight of one or more fatty substances,
  from 0.1% to 4% by weight of one or more gelling agents,
  from 7% to 15% by weight of one or more hydrating active agents,
  optionally from 0 to 3% by weight of one or more preservatives,
  optionally from 0 to 1% by weight of one or more pH adjusters, so as to maintain the pH at around 7, in particular between 6.5 and 7.5,
  water.

These compositions are particularly efficacious in the treatment of chemotherapy-induced neuropathic pain, since they make it possible not only to efficaciously treat the pain, but also to restore the skin that is often dehydrated at the painful extremities.

Preferably, the surfactant(s), the fatty substance(s), the gelling agent(s), the hydrating active agent(s), and the preservative(s) are as defined above.

Particularly preferably in this embodiment, the composition according to the invention comprises:
  from 10% to 30%, preferably from 10% to 20% by weight, more preferentially from 10.5% to 15% by weight of amitriptyline or of a pharmaceutically acceptable salt thereof,
  from 2% to 8% by weight of one or more surfactants chosen from sorbitan esters, glycerol esters, and mixtures of these compounds, or other surfactants allowing stabilization of the formula:

from 15% to 25% by weight of one or more fatty substances, including mineral oils, fatty acids, waxes and mixtures of these compounds, from 0.1% to 4% by weight of one or more gelling agents including carboxyvinyl polymers, from 7% to 15% by weight of one or more hydrating active agents, optionally from 0 to 3% by weight of one or more preservatives, optionally from 0 to 1% by weight of one or more pH adjusters, water.

Most particularly preferably in this embodiment, the composition according to the invention comprises:

from 10% to 30%, preferably from 10% to 20% by weight, more preferentially from 10.5% to 15% by weight of amitriptyline or of a pharmaceutically acceptable salt thereof, from 2% to 8% by weight of a mixture several non-ionic surfactants including one or more sorbitan esters and one or more glycerol esters, from 15% to 25% by weight of a mixture of one or more mineral oils, of one or more fatty acids and of one or more waxes, from 0.1% to 4% by weight of one or more carboxyvinyl polymers (carbomer), from 7% to 15% by weight of glycerol, optionally from 0 to 3% by weight of one or more preservatives, optionally from 0 to 1% by weight of one or more pH adjusters, water.

In particular, this embodiment makes it possible to reduce, or even eliminate, the side effects associated with the absorption of amitriptyline, in particular skin irritation at the site of application of the composition.

This embodiment also makes it possible to obtain good stability over time of the composition according to the invention at ambient temperature, but also at higher storage temperatures (45° C. for example).

Finally, this embodiment makes it possible advantageously to facilitate the penetration of the amitriptyline through the skin without passage into the bloodstream. The majority of the amitriptyline is concentrated in the dermis. Good therapeutic efficacy is thus obtained with good tolerance.

The pH of the compositions according to the invention is preferably between 5 and 8 and is adjusted with a base of NaOH or triethanolamine type.

The composition according to the invention is a topical composition.

The composition according to the invention may be in liquid, pasty or solid form, and more particularly in the form of salves, creams, milks, ointments. Preferably, the composition according to the invention is in the form of a light and unctuous cream.

The following examples illustrate the composition according to the invention and the advantages of this composition. However, they do not in any way represent a limitation of the present invention, but simply illustrate the invention.

EXAMPLES

Example 1

Composition in the Form of an Oil-In-Water Emulsion

| | |
|---|---|
| Amitriptyline | 10 mg |
| Glyceryl stearate | 1 mg |
| Other surfactants | 1 mg |
| Paraffinum liquidum | 12 mg |
| Palmitic acid | 1 mg |
| Stearic acid | 1 mg |
| Beeswax (cera alba) | 1 mg |
| Carbomer | 0.1 mg |
| Glycerol | 10 mg |
| pH adjuster qs | pH 6.9 |
| Preservative | qs |
| Water | qs 100 mg |

The cream thus obtained was applied, once in the morning and evening, to the painful zones of a population of 31 patients with chemotherapy-induced peripheral neuropathic pain. It was applied to the hands and the feet.

Among the patients treated, three groups were distinguished according to how long the neuropathic pain had been present.

Group GR1 (11 patients) was treated within a period of one month after the occurrence of the neuropathic pain. These patients feel neuropathic pain of moderate intensity (visual analogue scale, VAS=4/10) of the type electrical discharges, burning, pins and needles. Because of the occurrence of this debilitating pain, the chemotherapy doses had to be decreased in the majority of cases, the chemotherapy had to be stopped for 2 patients. The application of the amitriptyline cream above for 3 to 5 days is efficacious at 100% and totally reduces the pain (VAS 0/10). The treatment is stopped, without recurrence, after one month making it possible to re-initiate the chemotherapy or to re-increase the doses.

Group GR2, the patients (13) feel neuropathic pain of the extremities of moderate to severe intensity (VAS of between 5 and 7/10) of the type burning, electrical discharges, pins and needles, sensation "of oedema" of the affected zones. The application of the amitriptyline cream at 10% is efficacious (VAS 2 3/10) after 15 days of treatment. At one month, the pain disappeared (VAS 0/10) in all the patients. The patients treated for chemotherapy-induced neuropathies continue the treatment throughout the chemotherapy regimens as a preventive measure.

Group GR3, the patients (7) feel neuropathic pain of severe intensity (VAS greater than 7/10) of the type burning, electrical discharges, stabbing, pins and needles, sensation "of oedema" in the affected zones. The functional consequence is major (difficulty gripping when the hands are affected, difficulty walking when the feet are affected, impossible to put on closed shoes, difficulty putting on clothing on the affected zone) and the patients present a depressive syndrome associated with neuropathic pain. For the latter patient group, the 10% amitriptyline cream begins to be efficacious (loss of 3 VAS points) starting from one month of treatment. The treatment is continued for 3 months (VAS less than 2/10).

Example 2

Composition in the Form of an Oil-In-Water Emulsion

| | |
|---|---|
| Amitriptyline | 15 mg |
| Glyceryl stearate | 1 mg |
| Other surfactants | 1 mg |
| Paraffinum liquidum | 12 mg |
| Palmitic acid | 1 mg |
| Stearic acid | 1 mg |
| Beeswax (cera alba) | 1 mg |
| Carbomer | 0.1 mg |
| Glycerol | 10 mg |
| pH adjuster qs | pH 6.9 |
| Preservative | qs |
| Water | qs 100 mg |

The composition in the form of a cream was administered to patients experiencing neuropathic pain of severe intensity (VAS of greater than 7/10) of the type burning, electrical discharges, stabbing, pins and needles, sensation "of oedema" in the affected zones. The administration of the cream provides very good pain control in one month of treatment (VAS between 0 and 2/10).

Example 3

The cream of example 1 was applied, once in the morning and evening, to the painful zones of a population of 5 patients experiencing post-shingles peripheral neuropathic pain.

The patients feel neuropathic pain of the extremities of moderate to severe intensity (VAS between 6 and 8/10) of the type burning, electrical discharges, pins and needles, sensation "of oedema" of the affected zones. The application of the cream of example 1 to the thorax (4) and to the thighs (1) is efficacious (VAS 2 3/10) after 15 days of treatment. At one month, the pain disappeared (VAS 0/10) in all of the patients. The patients treated can stop the treatment.

Example 4

The following cream was prepared in the form of an oil-in-water emulsion:

| | |
|---|---|
| Amitriptyline | 10 mg |
| Glyceryl stearate | 2 mg |
| Sorbitan stearate | 1 mg |
| Paraffinum liquidum | 8 mg |
| Cetearyl ethylhexanoate | 5 mg |
| Palmitic acid | 1 mg |
| Stearic acid | 1 mg |
| Beeswax (cera alba) | 2 mg |
| Carbomer | 0.2 mg |
| Hydroxyethyl acrylate/sodium acryloyldimethyl taurate copolymer | 0.1 mg |
| Glycerol | 10 mg |
| pH adjuster qs | pH 6.9 |
| Preservative | qs |
| Water | qs 100 mg |

The cream was applied, once in the morning and evening, to the painful zones of a patient experiencing post-diabetic peripheral neuropathic pain.

The patient feels neuropathic pain of severe intensity (VAS of greater than 7/10) of the type burning, electrical discharges, stabbing, pins and needles, sensation "of oedema" in the affected zones. The functional consequence is major (difficulty gripping when the hands are affected, difficulty walking when the feet are affected, impossible to put on closed shoes, difficulty putting on clothing on the affected zone). The 10% amitriptyline cream begins to be efficacious (loss of 3 VAS points) starting from one month of treatment. The treatment is continued for 3 months (VAS less than 2/10).

Example 5

2 patients suffering from colon cancer and having R-CHOP therapy regimens as chemotherapy, who had experienced, after the 1st therapy regimen, severe neuropathy in the hands of the type pins and needles, very intense painful cold sensation, VAS 7 8/10, were treated. Faced with the intensity of the neuropathy, the 2nd R-CHOP therapy regimen had been put back.

7 days before the 2nd therapy regimen, the patients applied the 10% amitriptyline cream to the hands and continued the application for 7 days after the chemotherapy regimen without suffering from neuropathy (VAS 1 2/10 without painful cold sensation).

Example 6

Ex vivo study of the percutaneous amitriptyline absorption and of the presence of the pharmacologically active metabolite: nortriptyline.

A composition in the form of a cream containing 10% by weight of amitriptyline hydrochloride was applied to samples of human skin. The experiment was repeated 3 times with 3 samples of skin from 3 different donors, that is to say 9 samples. The skin samples are mounted in a Frantz cell and are brought to a surface temperature of 32° C.±1° C.

The formulation containing 10% by weight of amitriptyline hydrochloride by spreading it uniformly, using a spatula, on each skin sample in a proportion of 10 mg per cell, corresponding to 5 mg/cm2 of skin.

The skin samples are rinsed 16 hours after application.

Each skin sample was placed on absorbent paper (dermis facing downwards) with tweezers.

The stratum corneum is removed using adhesive tapes.

After removal of the stratum corneum, the sample is perforated. The epidermis is then separated from the dermis. Each one of them is placed in separate vials.

The various samples were then extracted.

These tests made it possible to note that 90.6% to 98% of amitriptyline remains at the surface of the skin. Approximately 74% of the amitriptyline is present in the dermis compared with 26% in the epidermis.

The amitriptyline bioavailability is 22.5 µg.

A passage into the bloodstream of less than 0.1% and a very low bioconversion of the amitriptyline into nortriptyline of about 25 ng were observed.

Example 7: In Vivo Studies

7.1 Methods

7.1.1 Patients

Patients with CIPN were recruited after being referred to the pain management department at the Necker Hospital (Paris, France) by their oncologist or hematologist. Patients with open lesions on the hands or feet, and those with dementia or who were incapable of applying the cream themselves, were not eligible. This study was conducted within the framework of the ongoing management of the patients and all patients gave oral consent before being included in the study.

Patients were instructed to apply 1 g (obtained using a measuring device) of 10% amitriptyline hydrochloride cream (oil-in-water emulsion), twice a day to each area with pain, burning, numbness, and/or tingling. They were told to apply the cream thinly and to rub it in gently, and to wait 30 minutes before handwashing. There was no need for foot washing after application of the cream. No other new or existing analgesics were to be used during the study period.

Neuropathic pain was assessed before and after 1 month of treatment using a validated scale from the neuropathic pain in 4 questions (DN4) questionnaire. Pain intensity was assessed at day 7, day 15 and month 1, using the Numeric Pain Rating Scale (NPRS). Patients were also asked to report any adverse events (AEs) at each visit.

Systemic availability of amitriptyline after topical administration was assessed by measuring the concentrations of amitriptyline and its metabolite, nortriptyline, in serum from patient blood samples drawn on Day 15. The plasma half-life of amitriptyline is 9-36 hours, and all blood samples were taken within 4 hours of the last application of the cream. Serum was extracted within 2 hours of the blood sample being drawn and proteins were removed by organic solvent precipitation. The supernatant was then removed and amitriptyline and nortriptyline were analysed by liquid chromatography coupled with tandem mass spectrometry (LC-MS/MS). The lower limit of detection for both compounds was 10 ng/mL.

7.1.2 Laboratory Animals

The mice used in this study were bred and housed in our accredited facilities; they were adult males, 6 to 12 weeks old, and from a C57Bl/6J background. The animals were kept in standard laboratory conditions with 12-hour light/dark periods at a temperature of 22±2° C. and supplied with dry food and drinking water ad libitum. All animals were handled in compliance with the European Community guidelines for the care and use of animals (86/609/EEC). Since pain might occur in these experiments, the guidelines of the Committee for Research and Ethical Issue of the International Association for the Study of Pain were followed. Furthermore, all procedures were approved by the institutional review board of the regional ethic committee (Region PACA).

7.1.3 Assessment of the Nociceptive Withdrawal Threshold in Mice Using the Randall-Selitto Test The nociceptive withdrawal threshold was assessed using a Randall-Selitto electronic algesimeter (Ugo Basil, Italy) following a protocol similar to that described by Santos-Nogueira et al, Randall-Selitto test: a new approach for the detection of neuropathic pain after spinal cord injury. J Neurotrauma, 2012. 29(5): p. 898-904. Before the test, each animal received 5 min of handling to get used to manipulation. The animal was placed into a soft cotton cloth and carefully immobilized with the same hand used to hold the tested paw. The test consisted of the application of an increasing mechanical force, in which the tip of the device was applied onto the medial portion of the dorsal surface of the hind paw until a withdrawal response was elicited. To allow for intra-individual variability between measurements, tests were performed every day for a period of four days prior to the application of a cream containing 10% amitriptyline or a control cream, (Excipial Hydrocreme®) to the test area of the hind paw. Tests were then repeated 5 min after application of the 10% amitriptyline or the control cream. At each time point, tests were conducted on eight mice in each group and the mechanical stimulation was repeated three times with a 15 min interval between consecutive tests.

7.1.4 Ex Vivo Single Unit Recordings from Mouse Skin-Nerve Preparations

Adult male mice were anesthetized with isoflurane (4%) and sacrificed by severing of the carotid arteries. Skin-saphenous nerve preparations and single-fiber recordings were carried out. The saphenous nerve and the skin of the hind limb were carefully dissected and placed in a custom-designed organ chamber containing warm oxygenated synthetic interstitial fluid (SIF). The SIF buffer had the following composition (in mM): 120 NaCl, 3.5 KCl, 0.7 $MgSO_4$, 1.7 $NaH_2PO_4$, 5 $Na_2HCO_3$, 2 $CaCl_2$, 9.5 Na-Gluconate, 5.5 glucose, 7.5 sucrose, and 10 HEPES. The pH was set to 7.4 and the osmolarity was maintained at 300 mOsm/L. The skin was placed corium side up in the organ bath, continuously superfused with SIF buffer and maintained at a temperature of 31° C. using a CL-100 temperature controller (Warner Instrument, Harvard apparatus, USA).

The saphenous nerve was placed in an adjacent recording chamber filled with mineral oil, gently teased, and groups of nerve fibers were placed on a gold recording electrode in order to isolate single-unit activity. Extracellular action potentials from single nerve fibers were recorded with a DAM 80 AC differential amplifier (WPI) and digital outputs were acquired using the CED Spike2 system (sampling rate of 20 kHz; Cambridge Electronic Design Limited, UK). Spikes were discriminated off-line using the Spike2 software (Cambridge Electronic Design Limited, UK) and analyzed individually to avoid false positives. The mechanically evoked activity of single saphenous nerve fibers was first obtained in response to von Frey hair stimulations (Friedrich-Alexander University, Erlangen, Germany). Once a receptive field had been characterized, a patch of skin was isolated from the surrounding bath using a plastic minichamber (inner diameter: 0.8 cm) continuously superfused with buffer at 31° C. The receptive field was then stimulated using von Frey mechanical probes mounted on the arm of a computer-controlled piezoelectric stepper (E-861 NEXACT® controller; PI, Germany). Conduction velocity was determined by electrically stimulating (Tungsten microelectrode: 10 mm ext/60 mm PI; FHC, USA) identified receptive fields with square wave pulses (0.1-0.5 ms, 7-15 V). Axons were considered to be A-type when the conduction velocity was over 4 m/s. Fibers with a conduction velocity below 1 m/s were classified as C fibers.

Recordings of mechanically induced firing of the A and C fibers were carried out in the absence of amitriptyline (control) and after superfusion of the skin preparation with amitriptyline for 5 min, 10 min and after a 30 min washout. Dose-responses were obtained by measuring firing activity after skin superfusion with amitriptyline (10-100 μM) for 10 min.

7.1.5 Culture of Mouse Dorsal Root Ganglion (DRG) Neurons

Cultures of DRG were prepared from male mice anesthetized with isoflurane (4%, Piramal Critical Care) and sacrificed by severing of the carotid arteries. Cultures of dissociated DRG neurons were established from thoracolumbar DRG.

DRG for whole-cell patch-clamp recordings were incubated in Hanks balance salt solution (Invitrogen, France) containing 2 mg/ml of collagenase IA (Sigma, France) for approximately 45 minutes at 37° C. DRG were washed at least 10 times and then triturated with a fired polished glass Pasteur pipette. Dissociated DRG neurons were cultured in Dulbecco's Modified Eagle Medium (DMEM; Invitrogen) supplemented with 10% heat-inactivated fetal calf serum, 50 U/mL penicillin-streptomycin, 2 mM L-glutamine, 25 mM glucose, 25 ng/mL nerve growth factor, and 2 ng/mL glial-derived neurotrophic factor (Invitrogen).

For calcium mobilization measurements, 10 DRG cultures (two mice per culture) were washed with Hanks Balanced Salt Solution (HBSS, Thermo Fisher Scientific, Massachusetts, USA), and incubated in HBSS containing 1 μg/ml papain (Sigma Aldrich, Missouri, USA) and L-cysteine (pH 7.4, Sigma Aldrich) for 10 minutes at 37° C. DRG were rinsed in Leibovitz's L-15 Medium (Thermo Fisher Scientific, Waltham, MA USA) containing 1% penicillin-streptomycin and 10% Fetal Bovine Serum (FBS) (Thermo Fisher Scientific) and digested twice with 4 mg/ml dispase II (Sigma Aldrich) and 1 mg/ml collagenase type I (Sigma Aldrich) for 10 minutes at 37° C. Neurons were then mechanically dissociated. After centrifugation at 50 g, neurons were plated into an eight-well Nunc™ Lab-Tek™ II CC2™ Chamber Slide System (Thermo Fisher Scientific, Massachusetts, USA) in DMEM containing 3% FBS, 1% penicillin-streptomycin and 10 μM of a cocktail of mitosis inhibitors including cytosine-β-D-arabinofuranoside, 5-fluorouracil, and uridine (Sigma Aldrich) for 24 h.

7.1.6 Transient Transfection of HEK293T Cells with hNav1.7 cDNA

Human embryonic kidney 293T (HEK293T) cells were grown in DMEM containing 4.5 mg/ml glucose, 10% FBS, 50 units/ml penicillin and 50 μg/ml streptomycin. Cells were plated onto 12-mm round glass poly-D-lysine-coated coverslips placed in 24-well plates and transfected using lipofectamine 2000 (Invitrogen) according to the manufacturer's instructions. hNav1.7 and GFP plasmids were co-transfected at a concentration of 600 and 100 ng/ml, respectively. Experiments were conducted on cells 24-48 hours post-transfection.

7.1.7 Whole-cell Patch-Clamp Recordings of Sodium Currents in DRG Neurons and Transfected Human Embryonic Kidney Cells Patch clamp recordings were made using borosilicate electrodes (Harvard Apparatus, Holliston, Massachusetts, USA) with a resistance of 2-3 MΩ when filled with an intracellular solution consisting of (in mM): 130 CsCl, 10 Hepes, 8 NaCl, 0.4 NaGTP, 4 MgATP, 1 MgCl2, 1 CaCl2 and 10 EGTA (adjusted to pH 7.3 with CsOH, ~300 mOsm/L). The bath solution had a lower concentration of sodium (in mM): 60 NaCl, 110 Sucrose, 3 KCl, 2.5 CaCl2, 1 MgCl2, 10 HEPES, and 10 glucose (pH 7.35, 300 mOsm/L). Voltage-gated sodium ion currents were leak-subtracted using a P/6 protocol and voltage errors were minimized using 75-80% series resistance compensation. Cultured cells were perfused with the bath solution at flow rate of 5 mL/min. Recordings were made at room temperature (20-24° C.) using an Axopatch 200B amplifier (Axon Instruments, Boston, Massachusetts, USA), filtered at 1-2 kHz, and digitally sampled at 5-20 kHz. Sodium currents were recorded individually. To record the tetrodotoxin (TTX)-resistant Nav1.8 and Nav1.9 currents in relative isolation, DRG neurons were bathed in a standard bath solution containing 300 nM TTX (to block TTX-sensitive Na+ currents) and 50 μM La3+ and 1 mM amiloride (to block voltage-activated Ca2+ currents). The Nav1.8 current was recorded in Nav1.9−/− DRG neurons, whereas the Nav1.9 current was recorded in Nav1.8−/− DRG neurons. Nav1.8−/− and Nav1.9−/− mice were generated from a C57B1/6J background. Fast activating/inactivating TTX-sensitive Na+ currents (Nav1.1 and Nav1.6) in putative non-nociceptors were recorded in wild-type DRG neurons that had large cell membrane capacitance (Cm>60 pF) and lacked any TTX-resistant Na+ current components. Nav1.7 recordings were made using the transfected HEK cells. All Na+ currents were recorded before and after cumulative addition of amitriptyline (1 μM-1 mM).

7.1.8 Treatment of Dorsal Root Ganglion Neurons for Measurements of Calcium Mobilization DRG neurons were incubated with HBSS containing 20 mM Hepes, 1 mM fluo-4 acetoxymethyl (AM) ester (Thermo Fisher Scientific, Waltham, MA USA) and 0.02% pluronic acid for 30 min at 37° C. followed by an additional incubation for 30 min at room temperature. The medium was then discarded and replaced by HBSS. Calcium mobilization in the DRG neurons was measured in response to increasing concentrations of amitriptyline (0.01 mM-1 mM) to obtain a dose response curve. The effects of TRP channel agonists and antagonists on amitriptyline-induced calcium ion mobilization were then assessed as follows: neurons were incubated with either an antagonist for TRPV1 (10 μM AMG 9810, Sigma Aldrich) or an antagonist for TRPA1 (HCO30031; Sigma Aldrich), or with the vehicle (0.001% DMSO HBSS) for 5 min before adding increasing amounts of amitriptyline or an agonist either for TRPV1 (62 nM capsaicin, Sigma Aldrich) or for TRPA1 (50 μM allyl isothiocyanate, AITC; Sigma Aldrich).

7.1.9 Calcium Imaging

Neurons were imaged using an inverted microscope (Zeiss) and a 10×0.5 NA objective. Images were acquired using a CCD camera (Zeiss) and Zen software (Zeiss). Acquisition parameters were kept constant during each experiment. Kinetic analysis was performed using 85 recordings (one per second). Baseline fluorescence was determined for 0 to 10 seconds, and then fluorescence was measured from the 10th to the 65th second after the neurons were incubated with the drugs or controls. At 65 seconds, 50 mM KCl was added to the cells in order to allow discrimination between neurons and glial cells. Variations in fluorescence intensity measured in each neuron were identified using Image J2 software.

7.1.10 Statistics

Data are presented as numbers and percentages, or means± the standard deviation (SD) or standard error of the mean (SEM). Statistical analyses were performed using the paired two-tailed t-test or nonparametric Mann-Whitney U and Wilcoxon tests as appropriate. Differences were considered significant if $p<0.05$.

7.2 Results

FIG. 1: Chemotherapy-induced hand and/or foot pain is alleviated by local 10% amitriptyline application.

Twenty patients with chemotherapy-induced neuropathic pain were treated with 10% amitriptyline hydrochloride cream, applied twice a day to each area with pain, for one month. Pain was assessed before and 1 month after treatment using both the Neuropathic pain in 4 questions (Douleur Neuropathique 4 Questions; DN4) questionnaire (see FIG. 1A) and the Numeric Pain Rating Scale (see FIG. 1B). Circles represent patient scores and each line represents one patient. Statistical analysis was performed using the Wilcoxon matched pairs test. ***p<0.001.

Figure 2:
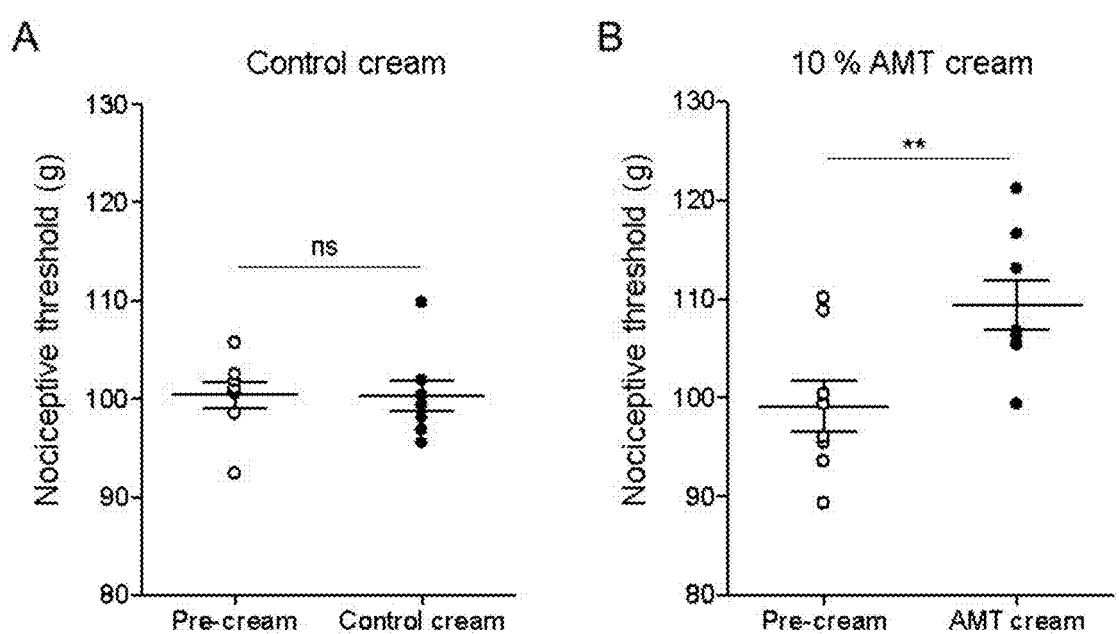
FIG. 2 effects of a single, 5-min skin application of a cream containing 10% amitriptyline on the nociceptive withdrawal threshold in mice.

FIG. 2: Effects of a single, 5-min skin application of a cream containing 10% amitriptyline on the nociceptive withdrawal threshold in mice. Nociceptive withdrawal thresholds were measured using a Randall-Selitto electronic algesimeter. Values were obtained for individual mice before and 5 min after application of a control cream (see FIG. 2A) or a 10% amitriptyline (AMT) cream (see FIG. 2B). Data are the means± SEM of measurements conducted in triplicate on eight mice from each group. ns, not significant; **p<0.01, Wilcoxon test.

Figure 3:
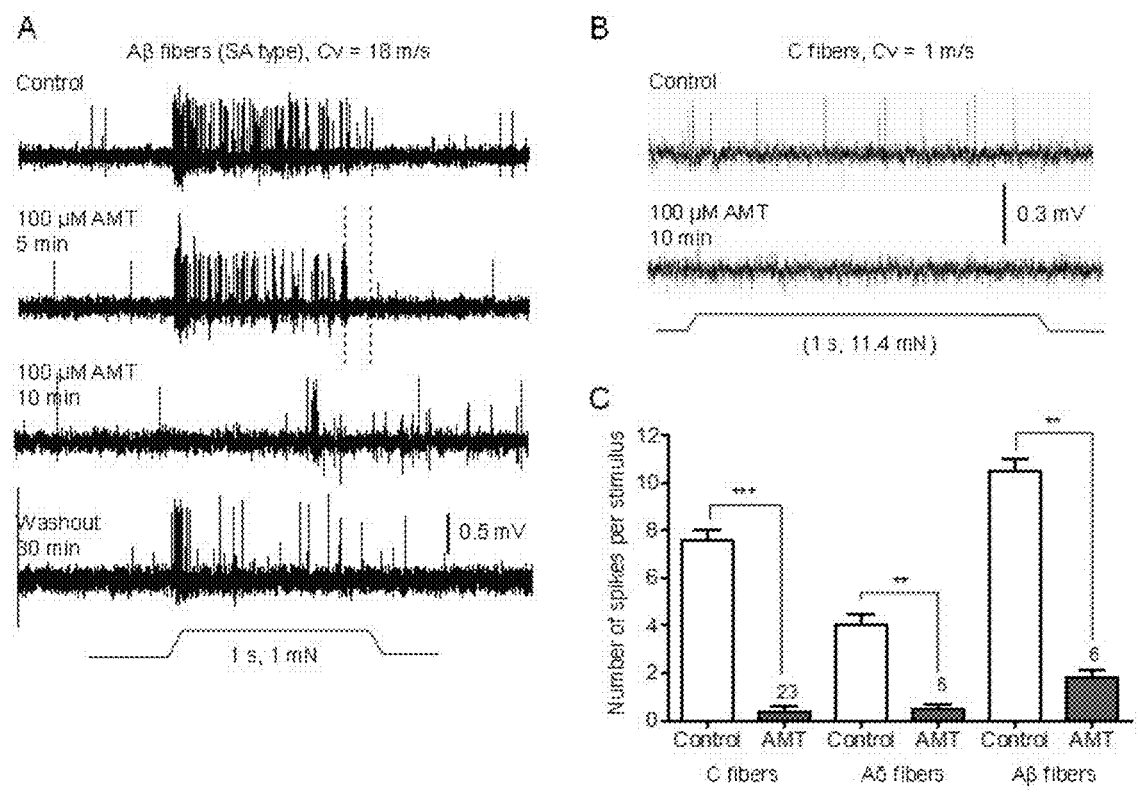
FIG. 3 amitriptyline applied to the skin reduces the mechanically induced activities of low-threshold mechanoreceptors and C-fiber nociceptors from the saphenous nerve.

FIG. 3: Amitriptyline applied to the skin reduces the mechanically induced activities of low-threshold mechanoreceptors and C-fiber nociceptors from the saphenous nerve. A. Discharge of a low-threshold Aβ (slow-adapting) mechanoreceptor in response to a 1 mN mechanical stimulus applied to the surface of the skin in the absence of amitriptyline (control), and after 5 and 10 min of skin superfusion with amitriptyline (100 μM). Note that inhibition was not complete and was partially reversed after a 30 min washout of amitriptyline. B. Full inhibition of firing in a C-type mechanonociceptor fiber in response to 11.4 mN mechanical stimulation in the absence of amitriptyline (control), and after 10 min of amitriptyline (100 μM) superfusion of the receptive field. Data presented are representative of 6 and 13 Aβ- and C-type fiber recordings, respectively C. Mean firing discharge of C, Aδ and Aβ sensory fibers before and after 10 min of skin superfusion with 100 μM amitriptyline. The number of recorded fibers is indicated. Data are expressed as means± SEM. AMT, amitriptyline; SA, slow-adapting; Cv, conduction velocity; p<0.01, Wilcoxon test *p<0.001, paired two-tailed t-test.

Figure 4:
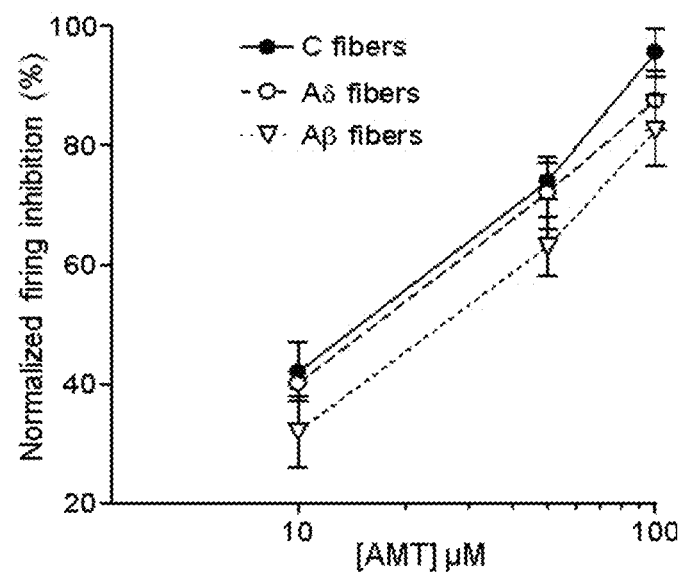
FIG. 4 nociceptive C and Aδ fibers are more susceptible to amitriptyline block than low-threshold Aβ fibers.

FIG. 4: Nociceptive C and Aδ fibers are more susceptible to amitriptyline block than low-threshold Aβ fibers. Dose-dependent effect of amitriptyline (AMT) on firing responses of single saphenous C, Aδ and Aβ sensory fibers (n=5 for each concentration). Each bar represents the mean inhibition expressed as a percentage of the control response. Approximate IC50 values were 15, 16 and 26 μM for C, Aδ and Aβ sensory fibers, respectively.

Figure 5:
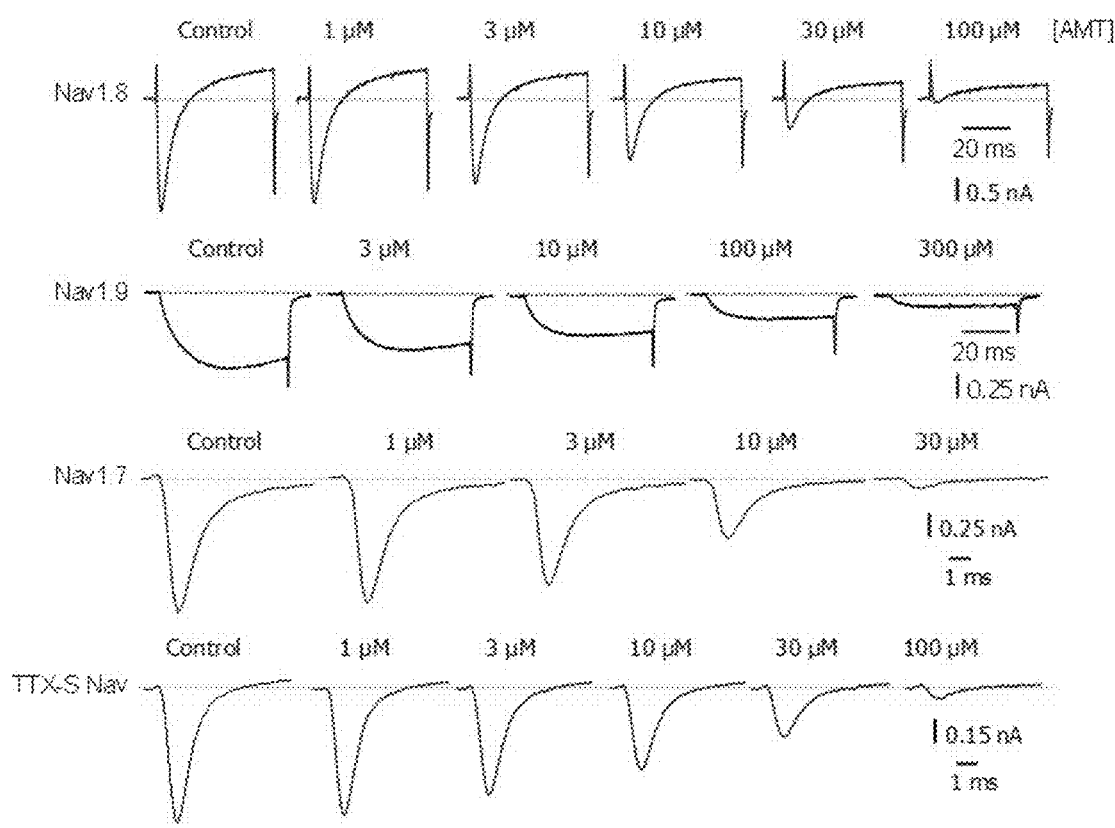
FIG. 5 amitriptyline inhibits all sodium channel isoforms from sensory neurons.

FIG. 5: Amitriptyline inhibits all sodium channel isoforms from sensory neurons. The effect of cumulative application of amitriptyline (AMT) on the current through Nav channels expressed in nociceptors (Nav1.8, Nav1.9 and Nav1.7) and the tetrodotoxin (TTX)-sensitive fast activating/inactivating Nav channels (TTX-S: mixture of Nav1.2 and Nav1.6) expressed in non-nociceptive sensory neurons. Currents were elicited by voltage steps from a holding potential of −100 mV (Nav1.8 and Nav1.9) or −80 mV (Nav1.7 and TTX-S Nav). Nav1.9 current was recorded in Nav1.8−/− DRG neurons, whereas Nav1.7 was recorded in hNav1.7-expressing human embryonic kidney cells. Data presented are representative of the recordings from seven measurements, except for Nav1.9 currents (n=5).

Figure 6:
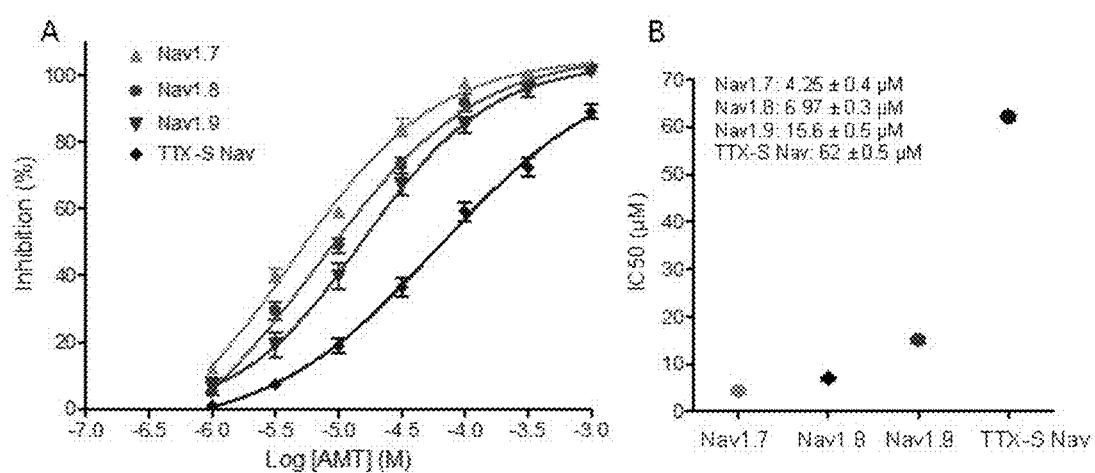
FIG. 6 amitriptyline shows a 10-fold selectivity for Nav1.8 and Nav1.7 over Nav1.1 and Nav1.6.

FIG. 6: Amitriptyline shows a 10-fold selectivity for Nav1.8 and Nav1.7 over Nav1.1 and Nav1.6.

FIG. 6A. Dose-response curves for amitriptyline (AMT) block of Nav currents. Dose-response curves were obtained by plotting the percentage inhibition at steady-state against the drug concentration. Data are expressed as means±SEM (n=5-7).

FIG. 6B. IC50 values for Nav1.7, Nav1.8, Nav1.9 and TTX-S Nav currents derived from the dose-response Hill curves shown in A. Note that amitriptyline shows a greater selectivity for nociceptor Nav channel isoforms (Nav1.7, Nav1.8 and Nav1.9) than for the TTX-S Nav channels (Nav1.1 and Nav1.6) present in non-nociceptive neurons.

Figure 7:
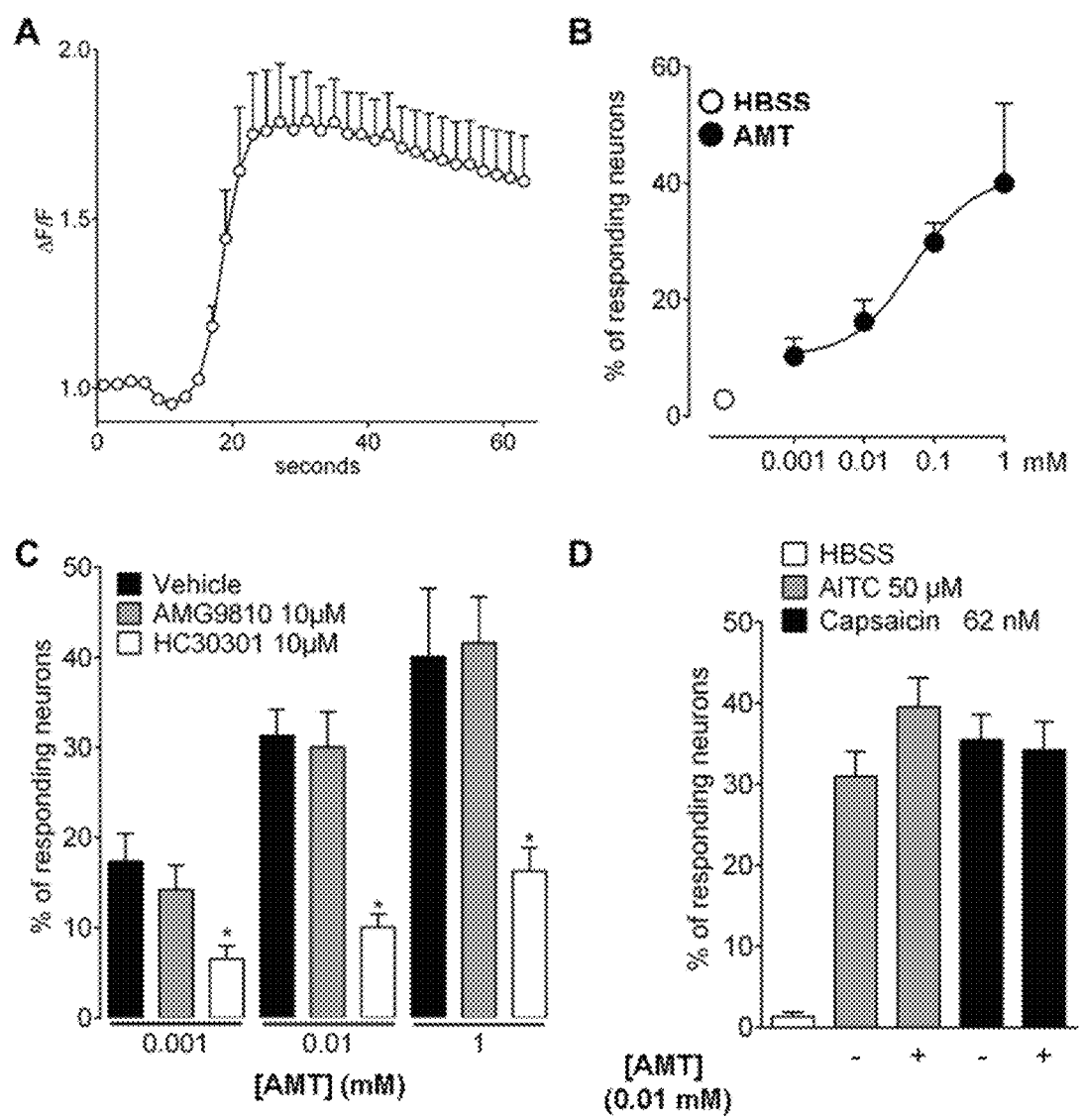
FIG. 7 Amitriptyline induces an increase in intracellular [Ca2+] in mouse sensory neurons through TRPA1.

FIG. 7: Amitriptyline induces an increase in intracellular $[Ca^{2+}]$ in mouse sensory neurons through TRPA1.

FIG. 7A. Representative Ca2+ flux measurements in DRG neurons exposed to 0.1 mM amitriptyline. ΔF/F was calculated as maximal fluorescence/baseline fluorescence. The baseline fluorescence was measured over a 10 second period before neuronal stimulation.

FIG. 7B. Dose-response curve showing the percentage of DRG neurons displaying intracellular calcium mobilization in response to increasing amounts of amitriptyline (black circles). As a control, the response to exposure to HBSS alone is also shown (white circle).

FIG. 7C Effects of a 5-min incubation with 10 μM AMG9810 (TRPV1 antagonist) or HC30301 (TRPA1 antagonist) on amitriptyline-induced Ca2+ mobilization in mouse DRG neurons.

FIG. 7D Effects of a 5-min incubation with 0.01 mM amitriptyline on Ca2+ mobilization induced by 62 nM capsaicin (TRPV1 agonist) or 50 μM allyl isothiocyanate (AITC; TRPA1 agonist) in mouse sensory neurons. Data are expressed as means±SEM of three independent experiments with two wells per condition and 60 to 80 neurons per well. *p<0.05 for the difference between antagonist-treated cells compared to cells incubated with the vehicle alone, according to the Mann-Whitney U test.

7.2.1 Effectiveness of 10% Amitriptyline Hydrochloride Cream in Patients with Chemotherapy-Induced Peripheral Neuropathy In total, 20 patients with hand and/or foot CIPN were included in the case series and treated for 1 month with a cream containing 10% amitriptyline. The baseline demographic and clinical characteristics of the patients are shown in table 1. The most common neuropathic chemotherapeutic agents were bortezomib (n=6; 30%) and oxaliplatin (n=4, 20%) and taxanes (n=4, 20%).

TABLE 1

Demographic and clinical characteristics of patients at baseline.

| Demographic and clinical characteristics | Patients N = 20 |
|---|---|
| Gender, n (%) | |
| Male | 8 (40) |
| Female | 12 (60) |
| Age (years) | |
| Mean ± SD | 60 ± 16.7 |
| Median (min-max) | 63 (8-82) |

TABLE 1-continued

Demographic and clinical characteristics of patients at baseline.

| Demographic and clinical characteristics | Patients N = 20 |
|---|---|
| Primary disease, n (%) | |
| Lymphoma | 5 (25) |
| Myeloma | 6 (30) |
| Colon/rectum cancer | 3 (15) |
| Breast cancer | 4 (20) |
| Sinus cancer | 1 (5) |
| Leukemia | 1 (5) |
| Neurotoxic agent, n (%) | |
| Oxaliplatin | 4 (20) |
| Cisplatin | 1 (5) |
| Cyclophosphamide | 1 (5) |
| Vincristine | 3 (15) |
| Vindesine | 1 (5) |
| Taxanes | 4 (20) |
| Bortezomib | 6 (30) |
| Time to CIPN onset (days) | |
| Mean ± SD | 96 ± 99.0 |
| Median (min-max) | 90 (0-365) |
| Duration of CIPN before treatment (months) | |
| Mean ± SD | 22 ± 35.3 |
| Median (min-max) | 6 (0-120) |

Abbreviations:
SD, standard deviation;
CIPN, chemotherapy-induced peripheral neuropathy On average, the patients had moderate-to-severe neuropathic pain at baseline with a mean DN4 score of 6/10, and were experiencing severe pain (NPRS score: 7/10; Table 2).

TABLE 2

Pain scores at baseline and after 1 month of treatment

| Pain scores | Baseline | 1 month |
|---|---|---|
| DN4 score (0-10) | | |
| Mean ± SD | 6 ± 1.7 | 3 ± 1.7 |
| Median (Min-Max) | 6 (4-9) | 3 (1-7) |
| NPRS score (0-10) | | |
| Mean ± SD | 7 ± 2.0 | 3 ± 2.1 |
| Median (Min-Max) | 8 (3-10) | 3 (0-7) |

N = 20, Abbreviations:
DN4, Douleur Neuropathique 4 Questions (Neuropathic pain in 4 questions);
NPRS, Numeric Pain Rating Scale;
SD, standard deviation.

The 1-month treatment with topical amitriptyline resulted in a 50% reduction in the mean DN4 score to 3/10 (Table 2 and FIG. 1A; P<0.001). In addition, reported mean pain intensity decreased from severe at baseline to mild after the 1-month treatment (NPRS score: 3: Table 2 and FIG. 1B; P<0.001).

Neither amitriptyline nor nortriptyline were detected in any of the patients for whom blood samples were taken during the course of the treatment (n=16). In addition, no local AEs (such as skin irritation), nor any of the frequent systemic AEs associated with oral amitriptyline use (notably xerostomia, dizziness or somnolence) were reported following application of the cream by the patients in our study.

7.2.2 Amitriptyline Administered Topically to the Skin Increases the Nociceptive Withdrawal Threshold in Mice We tested whether a cream containing 10% amitriptyline had analgesic/antinociceptive effects on the response thresholds to mechanical pressure stimulation in mice using the Randall-Selitto test with an electronic algesimeter. The nociceptive withdrawal threshold was assessed before and after a 5-min gentle massage with a control cream or a cream containing 10% amitriptyline. No difference in nociceptive withdrawal threshold was observed following treatment with the placebo control cream (FIG. 2A), whereas dorsal paw surfaces were significantly less sensitive to noxious stimuli following application of the 10% amitriptyline cream (FIG. 2B), with the mean nociceptive threshold value increasing by approximately 12% following application of the 10% amitriptyline cream.

7.2.3 Amitriptyline Inhibits the Activities of Both Nociceptive and Non-Nociceptive Nerve Fibers in Skin-Nerve Preparations The effects of amitriptyline on nerve fibers were evaluated by recording single unit activity from skin-saphenous nerve preparations from adult mice (FIG. 3). Low-threshold Aβ mechanoreceptors were identified as showing low mechanical thresholds (≤1 mN, n=6) with high conduction velocities (>20 m/s) and were identified as slowly adapting based on responses to constant force mechanical stimuli. C-type mechanonociceptive fibers were recognized as displaying high mechanical thresholds (range 11-32 mN, n=13) with low conduction velocities (≤1 m/s) and tonic activity. Aδ mechanonociceptive fibers were identified by their very high mechanical thresholds (>80 mN, n=6) and relatively high conduction velocities (3-14 m/s).

Exposure of the receptive field of both C-type mechanonociceptors and of low-threshold Aβ mechanoreceptors to 100 µM amitriptyline repressed mechanically-induced firing (FIGS. 3A and B). Mean inhibition of evoked firing after a 10 min application of 100 µM amitriptyline to the skin preparation was 95.6%, 87.5% and 82.5% in C, Aδ and Aβ fibers, respectively (FIG. 3C). Amitriptyline inhibition was dose-dependent with IC50 values of 15, 16 and 26 µM for C, Aδ and Aβ fibers, respectively (FIG. 4) and reversible within 30-35 min of washout.

7.2.4 Amitriptyline Inhibits Sodium Ion Channels in Sensory Neurons with Greater Potency Towards Nociceptor Channel Isoforms We investigated the effects of amitriptyline on Nav channels in sensory neurons from mouse DRG neurons recorded using the patch clamp technique. Nav channels including the Nav1.7, Nav1.8 and Nav1.9 isoforms are key to nociception, whereas other TTX-S Nav channel isoforms (Nav1.1 and Nav1.6) transmit non-noxious information. We found that amitriptyline applied at increasing concentrations inhibited these channels (FIG. 5). Inhibition by 100 µM amitriptyline was typically reversible within 20±2 min. Plotting the inhibitory effect versus amitriptyline concentration (FIG. 6A) yielded IC50 values of 4.25±0.4, 6.97±0.3 and 15.6±0.5 µM for Nav1.8, Nav1.7 and Nav1.9, respectively (FIG. 6B). Amitriptyline was 10-fold less potent (62±0.5 µM) at inhibiting TTX-S Nav currents of touch mechanoreceptors than the Nav1.8, Nav1.7 and Nav1.9 currents of nociceptive neurons (FIG. 6B).

7.2.5 Amitriptyline Activates Dorsal Root Ganglion Neurons Through TRPA1 Channels The effect of amitriptyline on calcium ion mobilization was investigated in primary cultures of mouse DRG neurons. Exposure to amitriptyline led to increases in the concentration of intracellular calcium ions within 10 seconds (FIG. 7A) and this effect was dose-dependent with an IC50 of 0.05 mM (FIG. 7B). The intracellular calcium ion amplitude curve reached a plateau after around 20 seconds of amitriptyline exposure (FIG. 7A), indicating that the response was associated with calcium ion channel opening. We therefore assessed whether amitriptyline-induced calcium ion mobilization was dependent on amitriptyline binding to TRPV1 or TRPA1 by pre-treating the cells with antagonists of these receptors. Pretreatment of the DRG neurons with an excess of TRPA1 antagonist (HC30301) led to inhibition of amitriptyline-induced calcium ion mobilization (FIG. 7C). In contrast, the pretreatment of neurons with an antagonist for TRPV1 (AMG9810) had no effect (FIG. 7C). We then assessed the ability of amitriptyline to facilitate the response of DRG neurons to stimulation. Addition of amitriptyline did not potentiate the activation of the DRG neurons induced by either a TRPV1 agonist (capsaicin) or a TRPA1 agonist (AITC) (FIG. 7D).

7.3 Discussion

This study showed that a 1-month topical treatment with 10% amitriptyline led to pain relief in a series of patients with CIPN, without amitriptyline being detected in the blood. Thus, high-dose (10%) topical amitriptyline has a local peripheral analgesic action and offers the potential to provide the same analgesic relief provided by oral amitriptyline but with minimal systemic AEs. It has been also demonstrated that amitriptyline applied to the skin repressed nocifensive behavior and dampened nociceptive C and Aδ afferent signaling in mice.

These findings indicate that topically applied amitriptyline acts through local peripheral inhibition of a variety of Nav channel subtypes, preferentially those expressed in nociceptors, and that amitriptyline induces calcium ion influx via TRPA1 channel activation.

7.3.1 Effectiveness of 10% Amitriptyline Hydrochloride Cream in Patients with CIPN The case series study involving 20 patients with hand and/or foot CIPN suggested that topical 10% amitriptyline cream, administered twice daily for 1 month, was effective at relieving the neuropathic pain induced by chemotherapy. The fact that no amitriptyline was found in patient blood samples after topical treatment confirms that 10% topical amitriptyline exerts its analgesic action by having a direct, local effect on the peripheral neuropathy.

In this study, no systemic AEs were reported. Although findings from some case studies have indicated high-dose amitriptyline creams are associated with an increased risk of systemic absorption and AEs, we found no evidence of systemic absorption of amitriptyline in blood samples, thus confirming the local analgesic action of the cream. No local AEs were reported by patients in this study.

7.3.2 Antinociceptive Action of Amitriptyline Cream in Mice

These in vivo experiments in mice demonstrated that amitriptyline cream could act on the peripheral nervous system, and was efficient at raising the nociceptive withdrawal threshold. These findings are in agreement with previous studies showing that amitriptyline applied to rodent paws can alleviate pain in animal models of neuropathic (nerve constriction injury) and inflammatory (formalin test) pain.

7.3.3 Amitriptyline Inhibits Nociceptive Afferent Messages by Targeting Sodium Channels These experiments on sensory fibers in an isolated mouse skin-saphenous nerve preparation indicate that amitriptyline, dose-dependently and reversibly, inhibited the evoked firing responses of the low-threshold Aβ-mechanosensory fibers and high-threshold C- and Aδ-sensory fibers that innervate the superficial layers of the mouse skin. Thus, as expected from its wide-ranging action on sodium ion channels, amitriptyline suppressed the activities of sensory afferents regardless of their sensory modality. However, the degree of block appeared to be slightly greater in nociceptive fibers than in Aβ-mechanosensory fibers. Amitriptyline block was also found to be dependent on nerve fiber activity.

Patch clamp-derived mechanistic analysis demonstrated that amitriptyline is a potent inhibitor of both TTX-sensitive and TTX-resistant Nav channels in DRG neurons, providing a potential mechanism of analgesia. Through its inhibitory action on Nav channels, amitriptyline dampens the excitability of sensory neurons and abolishes the firing activity of cutaneous sensory nerve fibers. The inhibitory effects were more potent for Nav1.7, Nav1.8 and Nav1.9, which are distributed in DRG nociceptors, than for Nav1.1 and Nav1.6, which are primarily found in non-nociceptive sensory neurons. The effect of amitriptyline was most potent on Nav1.7 and Nav1.8, with half-maximal inhibitory concentrations of 4.25±0.4 and 6.97±0.3 µM, respectively. Amitriptyline was also a very potent inhibitor of Nav1.9, which is strongly expressed in nociceptors and which contributes to the generation of a persistent inward current at subthreshold voltages. Thus, the broad selectivity of amitriptyline towards the nociceptor channels Nav1.7, Nav1.8 and Nav1.9 may prove to be a valuable characteristic, allowing topical amitriptyline to be an effective analgesic for a range of conditions.

7.3.4 Amitriptyline Induces Calcium Ion Influx by Activation of TRPA1

This study of the effect of amitriptyline on calcium ion mobilization revealed that amitriptyline increases the intracellular calcium concentration in sensory neurons via TRPA1 channel activation. TRPA1 is predominantly expressed in nociceptive C- and Aδ-type sensory neurons in DRGs and the trigeminal ganglia.

The precise role played by amitriptyline-induced TRPA1 activation in the action of amitriptyline remains to be determined. However, pungent natural compounds (mustard, clove, cinnamon, ginger etc.) that induce burning sensations are known to activate TRPA1, and burning skin irritation has been reported in a few studies as a local side effect of amitriptyline cream use. Sensitization of sensory neurons via activation of TRPA1 has already been implicated in injection site and postoperative inflammation and pain after use of local anesthetics. Although no local AEs were reported in this case series, one potential hypothesis is that TRPA1 activation may underlie the skin irritation induced by amitriptyline creams in rare patients.

7.4 Conclusion

The results of this case series study showed that the analgesic action of topical amitriptyline was mediated by local, rather than systemic effects on neuropathic pain. Thus, topical amitriptyline will have a much better profile for adverse effects compared to oral and parenteral routes as it relieves local pain with minimal systemic effects. The results of these studies in the mouse model provided insight into the mechanisms underlying the pain-relieving effects of amitriptyline cream in the patients with CIPN. Taken together these findings showed that topically administered amitriptyline displays antinociceptive action in peripheral tissues through potent inhibition of nociceptor voltage-gated sodium ion channels.

While illustrative embodiments have been illustrated and described, it will be appreciated that various changes can be made therein without departing from the spirit and scope of the invention.

The embodiment of the invention in which an exclusive property or privilege is claimed are defined as follows:

1. A pharmaceutical composition for the topical treatment of chemotherapy-induced peripheral neuropathic pain comprising, in a pharmaceutically acceptable carrier suitable for topical application, from 10.5% to 30% by weight, relative to the total weight of the composition, of amitriptyline or a pharmaceutically acceptable salt thereof, from 2% to 8% by weight of one or more surfactants chosen from sorbitan esters, glycerol esters, and mixtures of these compounds, —from 15% to 25% by weight of one or more fatty substances chosen from mineral oils, fatty acids, waxes and mixtures of these compounds, —from 0.1% to 4% by weight of one or more gelling agents chosen from carboxyvinyl polymers, —from 7% to 15% by weight of one or more hydrating active agents, —optionally from 0 to 3% by weight of one or more preservatives, —optionally from 0 to 1% by weight of one or more pH adjusters, and —water; wherein the amitriptyline or the pharmaceutically salt thereof is the sole agent for treating neuropathic pain.

2. Composition according to claim 1, for use in the treatment of chemotherapy-induced peripheral neuropathic pain, by application to the peripheral parts (hands and feet).

3. Composition according to claim 1, characterized in that it comprises from 10.5% to 20% by weight, relative to the total weight of the composition, of amitriptyline or of a pharmaceutically acceptable salt thereof.

4. A pharmaceutical composition for the topical treatment of chemotherapy-induced peripheral neuropathic pain comprising, in a pharmaceutically acceptable carrier suitable for topical application,
   from 10.5% to 30% by weight of amitriptyline or of a pharmaceutically acceptable salt thereof,
   from 2% to 8% by weight of a mixture of one or more sorbitan esters and of one or more glycerol esters,
   from 15% to 25% by weight of a mixture of one or more mineral oils, of one or more fatty acids and of one or more waxes,
   from 0.1% to 4% by weight of one or more carboxyvinyl polymers,
   from 7% to 15% by weight of glycerol,
   optionally from 0 to 3% by weight of one or more preservatives,
   optionally from 0 to 1% by weight of one or more pH adjusters, and
   water; wherein the amitriptyline or the pharmaceutically salt thereof is the sole agent for treating neuropathic pain.

5. Composition according to claim 1, characterized in that it is in the form of a cream.

* * * * *